United States Patent [19]
Cox, Sr.

[11] Patent Number: 5,415,546
[45] Date of Patent: May 16, 1995

[54] RADIOPAQUE DENTAL COMPOSITE AND MATERIALS

[76] Inventor: Ronald W. Cox, Sr., 6256 NE. 159th, Bothell, Wash. 98011

[21] Appl. No.: 35,447

[22] Filed: Mar. 23, 1993

[51] Int. Cl.$^6$ .................................................. A61C 11/00
[52] U.S. Cl. ...................................................... 433/213
[58] Field of Search .................. 433/202.1, 212.1, 213, 433/215

[56] References Cited

U.S. PATENT DOCUMENTS

| | | | |
|---|---|---|---|
| 3,539,526 | 11/1970 | Bowen | 260/41 |
| 4,220,582 | 9/1980 | Orlowski et al. | 260/42.28 |
| 4,375,967 | 3/1983 | Schaefer | 433/199 |
| 4,629,746 | 12/1986 | Michl et al. | 523/117 |
| 4,714,721 | 11/1987 | Franek et al. | 523/113 |
| 5,015,183 | 5/1991 | Fenick | 433/76 |
| 5,088,927 | 2/1992 | Lee | 433/224 |

OTHER PUBLICATIONS

Zinner, et al., "Presurgical Prosthetics and Surgical Templates," *Osseointegration* 33:619–632 (Oct. 1989).
Arlin, "Optimal Placement of Osseointegrated Implants," *J. Can. Dent. Assn.* 56:873–876 (Sep. 1990).
Steele, et al., "Stent–Aided Imaging for Osseointegrated Implants," *Oral Surg. Oral Med. Oral Pathol.* 70:243 (Aug. 1990).
Israelson, et al., "Barium–Coated Surgical Stents and Computer Assisted Tomography in the Preoperative Assessment of Dental Implant Patients," *Int. J. Periodont. Rest. Dent.* 12:53–61 (1992).
Mecall and Rosenfeld, "The Influence of Residual Ridge Resorption Patterns on Implant Fixture Placement and Tooth Position. Part II. Presurgical Determination of Prosthesis Type and Design," *Int. J. Periodont. Rest. Dent.* 12:33–51 (1992).
Adrian et al., "Trajectory Surgical Guide Stent for Implant Placement," *J. Prosthet. Dent.* 67:687–691 (1992).
Tarlow, "Fabrication of an Implant Surgical Stent for the Edentulous Mandible," *J. Prosthet. Dent.*, 67:217–218 (1992).

*Primary Examiner*—Cary E. O'Connor
*Attorney, Agent, or Firm*—Christensen, O'Connor, Johnson & Kindness

[57] ABSTRACT

Radiopaque dental compositions, radiopaque dental markers, and methods for making such markers are described, as well as kits containing combinations of, inter alia, the markers, molds for making the markers, and materials for sculpting the markers. The compositions contain a radiopaque material, for example diatrizoate sodium, in a polymeric binder. The markers may be in the shape of teeth, and can be sculpted or ground to conform to a patient's gingival surface and to occlude with an opposing tooth. The marker can then be placed in a stent for purposes of making radiographs of a patient's mouth from which an oral surgeon can determine the optimal placement of a permanent dental implant.

15 Claims, 2 Drawing Sheets

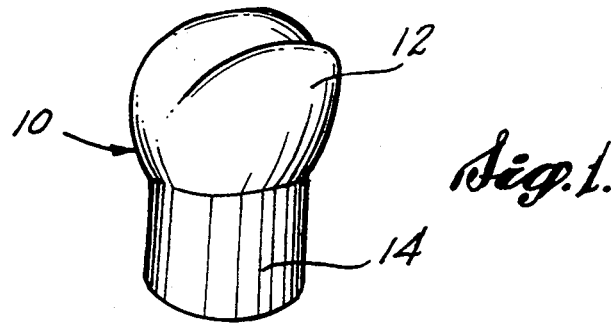
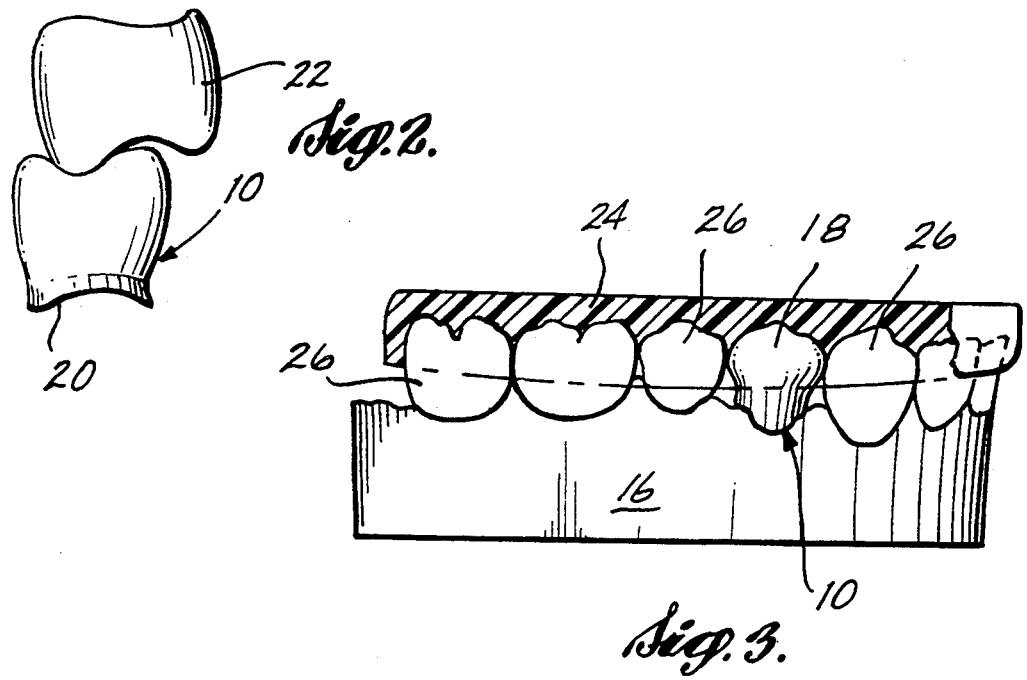
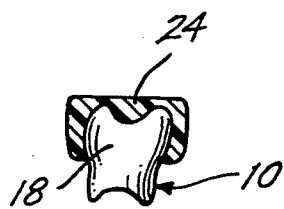
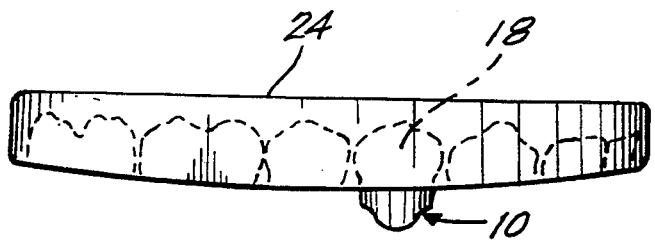

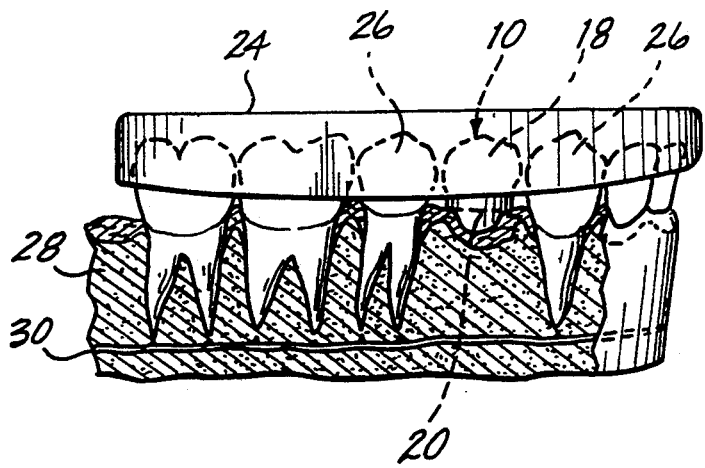
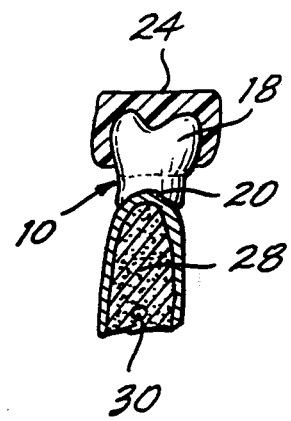
Fig. 6.   Fig. 7.
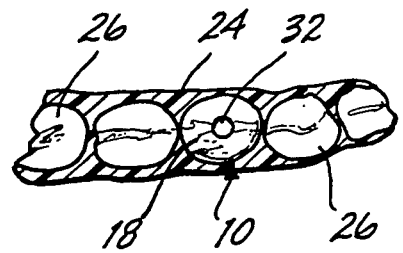
Fig. 8.
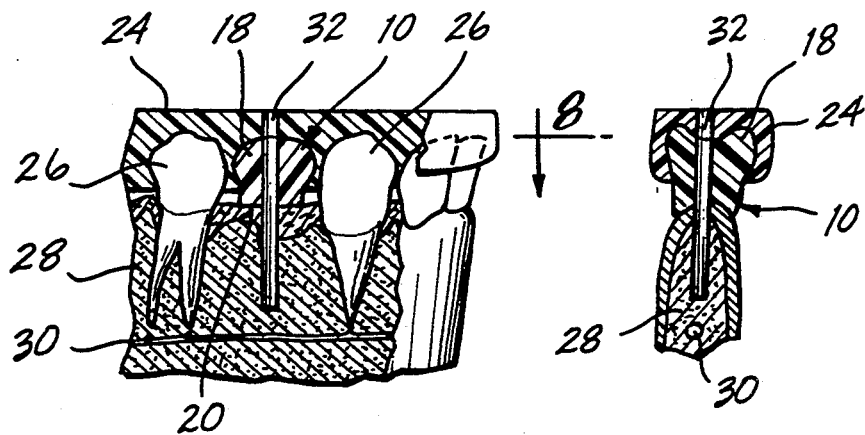
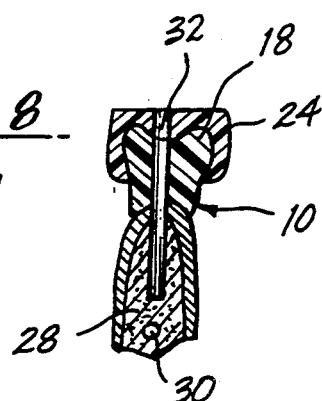
Fig. 9.   Fig. 10.

RADIOPAQUE DENTAL COMPOSITE AND MATERIALS

FIELD OF THE INVENTION

This invention relates to radiopaque compositions and devices made therefrom. In particular, this invention relates to a radiopaque composition made by combining a radiopaque material and a binder. The composition is molded into a radiopaque dental marker which may be in the shape of a tooth. The invention further relates to the method of making the markers as well as to kits containing, inter alia, the composition, molds, and/or finished, sculptable tooth-shaped radiopaque markers.

BACKGROUND OF THE INVENTION

Dental restoration is an important and highly technical subcategory of the dental specialty of prosthodontics. Many important and significant developments have occurred in this field since the days of President Washington and his set of wooden dentures. Although conventional cemented or removable prosthetic devices, for example, bridges, partial dentures, and complete dentures, are still used widely in dentistry, it is now more and more prevalent to find dental patients receiving permanently implanted individual replacement teeth. In many cases such permanent replacement teeth are preferred over removable prostheses, but at the present time the process involved in the actual fitting of permanently implanted replacement teeth is quite complicated and difficult to perform with accurate results.

The fitting of an implant-retained replacement tooth in place of a missing tooth in a patient's mouth requires several complicated steps. In order to anchor the replacement tooth in the patient's mouth, an implant must be placed into the patient's jaw. This implant will provide an anchoring device for the abutment(s) and screw(s) which will eventually hold the replacement tooth. However, it is difficult to properly locate sufficient maxillary or mandibular bone in which to fix the implant so that optimum security and positioning of the replacement tooth is achieved. Due to the fact that the bone structure and the density or mass of the underlying bone is not readily apparent on radiographs, implants are frequently positioned in a location where the bone structure is insufficient to form a proper anchoring position for the implant. This can ultimately lead to the failure of the implant. In addition, if the implant is seated at an improper angle an unaesthetic cosmetic appearance is achieved and, perhaps more importantly, improper occlusion results.

U.S. Pat. No. 5,015,183, issued to Fenick, partially addressed some of the earlier problems in the placing of such implants. That patent describes a method and device for placing an implant or artificial tooth in optimal bone structure by providing a radiology stent with a radiopaque grid contained within the stent. The stent is placed in the vicinity of the void where the implant is to be placed. A series of x-rays at oblique angles at spaced intervals along the implant provides grid points for determining the optimum trajectory of the proposed implant. The angles are then related to a formed surgical stent having a guide for directing a drill bit in the direction established by the radiology stent. In this device, and in other devices typically used in determining angle of placement of abutments for implants, metal wires serve as the radiopaque materials. Alternatively, in some cases, metal spheres may also serve as radiopaque markers. A principal disadvantage of the use of metal in x-ray radiography is that the metal can introduce distortional artifacts on the final radiograph. When angle of drilling trajectory is calculated based upon x-ray radiographs, such distortion can introduce significant error. As noted above, such error can lead to placement of abutments in bone of less than optimal mass or density, and/or at improper angles.

In addition, positioning of radiopaque metal wires or spheres in a stent such as that described in U.S. Pat. No. 5,015,183 does not provide an optimally accurate positioning vis-a-vis the gingival surface and the base of the replacement tooth. This can introduce further drilling error, further seating error, and once again can lead to a less than optimal anchoring of the replacement tooth. Furthermore, use of such a stent cannot provide an optimally accurate indication of the ultimate anatomical configuration of the replacement tooth. Without a knowledge of this final configuration, the best drilling angle may still not be achieved, and the best occlusal positioning may not be possible. This is due to the fact that peculiarities of tooth shape, occlusal angles, etc., in the final replacement implant may be such that an oral surgeon cannot use the most advantageous drilling angles for that particular tooth, even if those angles have been correctly calculated. Using a stent such as those known in the prior art in determining those drilling angles does not allow an oral surgeon to appropriately compensate for anatomical peculiarities.

Additionally, the method of making tooth-shaped forms currently recognized in the art is a complicated process involving several steps. First, the patient's dentist would make an impression of the patient's teeth. That impression would then be provided to a laboratory technician who would make stone models based upon the impression. The replacement teeth would then be designed and fabricated in wax from the stone mold. This multi-step process introduces error and variance in the size, shape, and most importantly in the occlusal conformation of the replacement tooth. It is also a time-consuming operation and an especially inefficient means of making forms for individual teeth.

Therefore, a significant need exists for a reference device for radiography that will provide a more accurate determination of proper drilling angles for better positioning of implants, and which does not create the distortion of x-ray images which can be generated by metallic objects. Ideally, such a reference device would be tooth shaped and would be made of a material which could be easily sculpted or modified in shape after it is molded so that it can serve not only as a radiopaque reference device for determination of drilling angles on a radiograph, but also as an accurate indicator of the final anatomical form and shape of the replacement tooth. The latter advantage would allow an oral surgeon to interpret simultaneously not only the proper angles for drilling vis-a-vis the underlying bone structure but also to take into account any peculiarities in the tooth shape which might require adjustment of those angles for the final drilling process.

SUMMARY OF THE INVENTION

The present invention addresses these problems by providing radiopaque compositions which can be molded into a tooth-shaped radiopaque dental marker or reference device, as well as the tooth-shaped radiopaque markers themselves. The marker can be sculpted or modified in shape to provide for the determination of optimal drilling angles on x-rays, and at the same time allow for adjustments based upon occlusal surface angles and peculiarities of tooth confirmation. Furthermore, the makeup of the radiopaque composition is such that the reference device can be modified to a surgical guide which can be drilled through in situ, thereby allowing for optimal placement of permanent implants. The invention also relates to a method of making radiopaque dental markers in the shape of teeth, and to kits containing, in various embodiments, combinations of the composition, molds for the markers, premolded dental markers, drill bits, and tools for shaping and modifying the markers. Premolded markers can be in the shape of teeth or in the shape of balls or spheres.

The radiopaque marker of the present invention comprises a moldable, sculptable radiopaque compound molded in the shape of a tooth, or, alternatively, in the shape of a ball or sphere. The marker can take the general shape of any tooth, for example, a molar, a cuspid, a bicuspid, or an incisor. The compound comprises a radiopaque material, for example, diatrizoate sodium, barium sulfate, iodine, or barium, and a binder, for example urethane, acrylic, or epoxy. The radiopaque material will, in one embodiment, comprise from about 10% to about 80% weight/volume (w/v) of the compound; in a preferred embodiment from about 15% to about 70% (w/v); and in a currently most preferred embodiment, from about 20% to about 60% (w/v) of the compound.

Tooth-shaped markers can be molded with hemispherical bases, for point-to-point contact with the gingival surface of a patient, or with lengthened bases which can be sculpted or ground to abut the edentulous ridge of a patient. Either variation of the method allows an oral surgeon to determine the optimal drilling parameters for implant placement. The marker can be further sculpted for proper occlusion with opposing teeth.

The kits of the present invention comprise combinations of at least two tooth-shaped dental markers, at least one in the general shape of a first type tooth, and at least one in the general shape of a second type tooth. The teeth included will be selected from the general types of teeth noted above. In additional alternative embodiments, the kits can also include molds for making markers, along with materials for making the composition of the invention, stabilizing struts for making stents for use in a patient's mouth, and instruments for sculpting, grinding and/or drilling the markers, and combinations thereof.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 shows a front elevational view of a radiopaque marker of the invention;

FIG. 2 shows a front view of a marker placed in proximity to an opposing tooth;

FIG. 3 shows a side view, partially in cross-section, of a stone model in which a marker has been placed for construction of a stent;

FIG. 4 shows a side view of a marker in a stent ready for placement in a patient's mouth;

FIG. 5 shows a front view, partially in cross-section, of a marker in a stent ready for placement in a patient's mouth;

FIG. 6 shows a side view of a marker in a stent as it would appear on a radiograph of a patient's mouth;

FIG. 7 shows a front view, partially in cross-section, of a marker in a stent as it would appear on a radiograph of a patient's mouth;

FIG. 8 shows a top view, partially in cross-section, of a marker in a stent which has been drilled for use in oral surgery as it would appear in a radiograph of a patient's mouth;

FIG. 9 shows a side view, partially in cross-section, of the drilled marker in a stent shown in FIG. 8; and FIG. 10 shows a front view, partially in cross-section, of the drilled marker in a stent shown in FIG. 8.

DETAILED DESCRIPTION OF THE PREFERRED EMBODIMENTS

The radiopaque dental marker of the present invention comprises a sculptable radiopaque compound which is molded into the general shape of a tooth or sphere and then hardened or cured. The compound, as discussed below, comprises a radiopaque material and a binder. The molded radiopaque marker can take the form of any of the teeth found in the human mouth, or the form of any tooth of any dentulous animal. In a preferred embodiment of the marker, the radiopaque material used in the formation of the marker is diatrizoate sodium. In a further preferred embodiment, the base of the marker is rounded or hemispherical, so that the marker, when placed in a radiopaque stent, makes a single point of contact with the surface of the gingiva of the patient. In an alternative preferred embodiment, the radiopaque dental marker is molded so that the length of the base of the marker is elongated. The base of the marker is then ground to fit precisely over the edentulous ridge of a particular patient. In either case, the use of the marker allows an oral surgeon to precisely determine, from a radiograph or a radiographic series, the depth of the gingival tissue between the base of the marker and the underlying bone, as well as the relationship between the marker (and ultimately the permanent implant) and the underlying bone in which the implant must be anchored.

In a particular embodiment, the radiopaque composition comprises a polymeric binding material combined with a radiopaque material. In a preferred embodiment the radiopaque material is diatrizoate sodium. Other radiopaque materials can be used, however, including, for example, barium sulfate, iodine, barium, or mixtures thereof. In one embodiment of the radiopaque composition, the radiopaque material comprises from about 10% to about 80% weight/volume (w/v) of the composition. In a preferred embodiment, the radiopaque material comprises from about 15% to about 70% w/v, and in currently most preferred embodiments from about 20% to about 60% w/v of the composition. In one embodiment, the binding material is a dental acrylic, for example, a tooth color, cold cure, acrylic resin, such as methyl methacrylate. In an alternative embodiment, the binding material is an epoxy. In a currently preferred embodiment, diatrizoate sodium (e.g., HYPAQUE ™, Winthrop Pharmaceuticals) is mixed with urethane in order to arrive at the radiopaque composition of the invention.

The present invention also relates to a method of making a radiopaque dental marker in the shape of a tooth for radiographic purposes. The following exemplary steps may be followed in a preferred embodiment of the method of the invention: First, a moldable radiopaque compound comprising a radiopaque material and a binder is mixed. The radiopaque compound is then poured into a wax mold, preferably in the shape of a tooth (for example, a human tooth), alternatively in the shape of a ball or sphere. The molded material is allowed to cure and dry, and is then removed from the mold. As discussed above, the moldable radiopaque compound is, in a preferred embodiment, a combination of diatrizoate sodium and urethane or an acrylic (e.g., methylmethylacrylate) or an epoxy. Alternatively, the moldable radiopaque compound can be a mixture of barium sulfate and urethane or an acrylic or an epoxy. Of course, other materials having similar desired characteristics may also be used. The method can also be refined so that the gingival base of the radiopaque marker is rounded or in a pear or hemispherical shape, such that after the marker is modified in shape, the base of the marker will make point-to-point contact with the surface of the gingiva in such a way as to allow an oral surgeon to determine, from a radiograph or a radiographic series, the optimal drilling site and angles for implant placement. Alternatively, the method can involve the molding of a marker having a base lengthened sufficiently to allow the base to be ground to fit precisely over the edentulous ridge of a patient. The method of the present invention also can be refined to include the modification of the shape of the dental marker so that a proper occlusion will occur with the opposite tooth of the patient, and so that the marker bears a conformation approximating that of the final implant. A stent can then be made which includes the ground, sculpted marker and a nonradiopaque stabilizing strut. The stent can then be placed in a patient's mouth and a radiograph (or a series of radiographs) can be made which allow an oral surgeon to determine the optimal drilling site and angle for placement of a permanent implant. The oral surgeon can also make judgments regarding adequate adjustments for the tooth's positioning peculiarities in the process of surgically placing the implant.

The present invention also relates to kits comprising radiopaque dental markers for radiography. In one embodiment of such a kit, at least two such dental markers are included, at least one in the general shape of a first type tooth, and at least one in the general shape of a second type tooth, the markers being independently selected from the group consisting of, for the maxillary teeth, right and left central incisors, tight and left lateral incisors, right and left cuspids, a bicuspid capable of use on either the right or left side, a right molar, and a left molar. For the mandibular teeth, the markers are independently selected from the group consisting of an incisor capable of use on the right or left and in either the central or lateral position, a right cuspid, a left cuspid, a bicuspid capable of use on either the right or left side, a right molar, and a left molar. In alternative embodiments, the teeth will be of a small or a large size, and in all cases the bicuspids and the mandibular incisor will be of a more generic shape. The kits, in alternative embodiments, also comprise combinations including additional teeth. In addition, alternate embodiments of the kits also comprise various combinations of the following: molds for making the radiopaque dental markers along with an amount of the elements of the radiopaque compound of the present invention, as well as stabilizing struts for the construction of stents containing one or more of the radiopaque dental markers, and instruments for sculpting and drilling the markers, for example, an acrylic cutting burr and/or dental drill bits.

The foregoing may be better understood in connection with the following examples:

EXAMPLE 1

Fabrication of Markers

Tooth-shaped radiopaque markers 10, as shown in FIG. 1, may be fabricated by making models of various teeth, such as, for example, centrals, laterals, cuspids, premolars and molars, both maxillary and mandibular. As can be seen in FIG. 1, the models of teeth may be designed so that, after a mold is constructed from the model and the marker is cast, the marker has a crown portion 12 (the portion of the tooth that is seen visually in the oral cavity) as well as an elongation of the root portion 14 of the tooth. A technician, dentist, or oral surgeon can modify the marker 10 to fit precisely to a space in the oral cavity, where teeth have been lost and implants are indicated, and to properly occlude with the opposite tooth 22, as shown in FIGS. 2 and 3. Once the desired shape of the model tooth is achieved, a mold is made from a flexible material (for example, polyvinyl siloxane). A radiopaque material, in this example diatrizoate sodium (HYPAQUE ™, Winthrop Pharmaceuticals), and binder were mixed, as described in Table 1, and poured into the polyvinyl siloxane mold, and allowed to cure. Curing can take place at room temperature, or at elevated temperature and pressure. The marker 10 is then extracted from the mold for use in fabrication of a stent 18, as shown in FIG. 3.

TABLE 1

| Amount of Binder* | Amount of HYPAQUE ™ | Radiopacity |
| --- | --- | --- |
| 5 ml | 0.5 gm | slight |
| 5 ml | 1 gm | optimal |
| 5 ml | 2 gm | optimal |
| 5 ml | 3 gm | optimal |
| 5 ml | 3.5 gm | very opaque** |

*Urethane, acrylic or epoxy.
**Quite thick.

EXAMPLE 2

Fabrication of a Stent

An impression is taken of a patient's maxilla and/or mandibular arch. As shown in FIG. 3, a stone model 16 is made from this impression. A radiopaque stent 18 is then fabricated on this stone model 16. For purposes of this example a single marker 10 is selected from an assortment based on the tooth to be replaced. The marker 10 is modified or shaped with an acrylic cutting burr to fit in the designated area. As shown in FIGS. 3 and 7, it is important that the marker 10 fit precisely to the edentulous ridge 20 and be in proper occlusion with the opposing tooth 22. The marker 10 should replicate the optimum position of the final prosthesis with cosmetic and functional concerns foremost in mind. Alternatively, the marker may take the form of balls or spheres of appropriate size (for example, 2-5 mm diameter) (not shown), in which case the sphere should make point-to-point contact with the gingival surface 20 at a point approximately midway between the adjacent teeth 26.

It is necessary for the marker 10 to be suspended in this position during the course of radiographs and surgery. A stabilizing strut 24, as shown in FIGS. 4 and 5, is fabricated over the marker 10 and the adjacent teeth 26. This secures the marker 10 in a fixed position, as shown in FIGS. 6 and 7. This enables one to transfer the stent 18 from the stone working model 16 to the patient's mouth with utmost accuracy. The stabilizing strut 24 is made from nonradiopaque materials, for example, methylmethacrylate or bis-GMA (light cure resin). The stent 18 is initially used to provide a reference point, visible on radiographs, to evaluate the amount and position of the underlying bone 28 and the position of the underlying nerve 30. As shown in FIGS. 6 and 7, the stent 18 is placed in the patient's mouth, and pertinent radiographs are made. The radiopaque markers 10 are visible on the radiographs, and measurements are made from the radiographs to determine maximal length of implant, and the implant angulation and position.

After using the stent 18 to determine ideal implant length, position and angulation from the radiographs, the stent 18 can be modified in several ways to act as a guide in helping the surgeon accurately place the implant. For example, as shown in FIGS. 8-10, a hole 32 can be drilled through the tooth-shaped marker 10 at the appropriate angle and in the optimal position on the tooth-shaped marker 10 to guide the oral surgeon's drill to allow for alignment of the implant with the roots of the adjacent teeth 26, and to allow for placement of the implant in the area of maximum bone density. This radiopaque tooth-shaped marker 10 included in the stent 18 eliminates duplication of effort, since one stent can be used both for radiographic marking and for surgical guidance during implant placement.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A radiopaque dental marker comprising a moldable, sculptable radiopaque composition, molded in the shape of a tooth, the radiopaque composition comprising from about 10% to about 80% (w/v) of a radiopaque material selected from the group consisting of diatrizoate sodium, barium sulfate, iodine, or barium or mixtures thereof and a binder selected from the group consisting of urethane, acrylic, or epoxy polymers.

2. The radiopaque dental marker of claim 1, wherein the radiopaque material comprises from about 15% to about 70% (w/v) of the radiopaque compound.

3. The radiopaque dental marker of claim 1, wherein the radiopaque material comprises from about 20% to about 60% (w/v) of the radiopaque compound.

4. The radiopaque dental marker of claim 1, wherein the marker is in the general shape of a molar, a bicuspid, a cuspid, a lateral incisor, or a central incisor.

5. The radiopaque dental marker of claim 4, wherein the marker is intended for use in the upper jaw.

6. The radiopaque dental marker of claim 4, wherein the marker is intended for use in the lower jaw.

7. A method of making a radiopaque dental marker in the shape of a tooth for radiography, the method comprising the following steps:

(a) mixing a moldable radiopaque material with a dental binder to form a moldable mixture;

(b) molding the mixture into a dental marker in the shape of a tooth having a gingival base in the shape of a hemisphere, the marker having a base of sufficient size to be shaped and conformed to abut a patient's edentulous ridge; and (c) hardening the molded radiopaque dental marker.

8. The method of claim 7, further comprising the steps of:

(d) modifying the radiopaque dental marker so that the base of the marker will make continuous or single point contact with the gingiva of a patient; and (e) modifying the occlusal surface of the marker so that a proper occlusion will occur with the opposite tooth of the patient.

9. The method of claim 7, further comprising the step of:

(f) adding a nonradiopaque stabilizing strut to the radiopaque dental marker.

10. A kit comprising at least two radiopaque dental markers for radiography, at least one in the general shape of a first type tooth, and at least one in the general shape of a second type tooth, wherein the dental markers comprise a moldable, sculptable radiopaque composition having from about 10% to about 80% (w/v) of a radiopaque material selected from the group consisting of diatrizoate sodium, barium sulfate, iodine, or barium, or mixtures thereof, and a binder selected from the group consisting of urethane, acrylic, or epoxy polymers.

11. The kit of claim 10, wherein the radiopaque dental marker in the general shape of a first type tooth and the radiopaque dental marker in the general shape of a second type tooth are independently selected from the group consisting of a molar, a bicuspid, a cuspid, a lateral incisor, or a central incisor.

12. The kit of claim 10, wherein the radiopaque dental marker in the general shape of a first type tooth and the radiopaque dental marker in the general shape of a second type tooth are independently selected from the group consisting of a left maxillary molar, a right maxillary molar, a maxillary bicuspid, a left maxillary cuspid, a right maxillary cuspid, a left maxillary lateral incisor, a right maxillary lateral incisor, a left maxillary central incisor, a fight maxillary central incisor, a left mandibular molar, a right mandibular molar, a mandibular bicuspid, a left mandibular cuspid, a fight mandibular cuspid, or a mandibular incisor.

13. A kit comprising at least two radiopaque dental markers for radiography, at least one in the general-shape of a first type tooth, and at least one in the general shape of a second type tooth, wherein the dental markers comprise a moldable, sculptable radiopaque composition having from about 10% to about 80% (w/v) of a radiopaque material selected from the group consisting of diatrizoate sodium, barium Sulfate, iodine, or barium or mixtures thereof, and a binder selected from the group consisting of urethane, acrylic, or epoxy polymers, and molds for the radiopaque dental markers.

14. The kit of claim 13, further comprising nonradiopaque stabilizing struts for construction of a stent containing at least one radiopaque dental marker.

15. The kit of claim 14, further comprising means for modifying the shape of and means for drilling the radiopaque dental markers.

* * * * *

UNITED STATES PATENT AND TRADEMARK OFFICE
CERTIFICATE OF CORRECTION

PATENT NO. : 5,415,546
DATED : May 16, 1995
INVENTOR(S) : R.W. Cox

It is certified that error appears in the above-indentified patent and that said Letters Patent is hereby corrected as shown below:

| COLUMN | LINE | |
|---|---|---|
| 5 | 51 | "tight" should read --right-- |
| 6 | 31 | "room 10 temperature" should read --room temperature-- |
| 8 (Claim 12, | 47 line 9) | "fight" should read --right-- |
| 8 (Claim 12, | 47 line 11) | "fight" should read --right-- |
| 8 (Claim 13 | 58 line 8) | "Sulfate," should read --sulfate,-- |

Signed and Sealed this

Tenth Day of October, 1995

Attest:

BRUCE LEHMAN

Attesting Officer    Commissioner of Patents and Trademarks